United States Patent
McLellan et al.

(10) Patent No.: US 8,337,786 B2
(45) Date of Patent: Dec. 25, 2012

(54) MICROSCOPE SLIDE COVER WITH INTEGRATED RESERVOIR

(75) Inventors: Andrew McLellan, Surrey Hills (AU); George Goris, Beaconsfield (AU); Chester Henderson, Mount Waverley (AU); Jonathan McKinlay, Hawthorn East (AU)

(73) Assignee: Leica Biosystems Melbourne Pty Ltd, Mount Waverly (AU)

( * ) Notice: Subject to any disclaimer, the term of this patent is extended or adjusted under 35 U.S.C. 154(b) by 0 days.

(21) Appl. No.: 12/561,468

(22) Filed: Sep. 17, 2009

(65) Prior Publication Data

US 2010/0002293 A1 Jan. 7, 2010

Related U.S. Application Data

(62) Division of application No. 10/518,478, filed as application No. PCT/AU03/00778 on Jun. 20, 2003.

(30) Foreign Application Priority Data

Jun. 20, 2002 (AU) .................................. PS3090/02

(51) Int. Cl.
*B01L 9/00* (2006.01)
(52) U.S. Cl. ........ 422/565; 422/547; 422/550; 422/551; 436/180
(58) Field of Classification Search .................. 422/102, 422/104, 547, 550, 551, 565, 568; 435/288.3, 435/288.4; 436/180
See application file for complete search history.

(56) References Cited

U.S. PATENT DOCUMENTS

| | | | |
|---|---|---|---|
| 3,141,547 A * | 7/1964 | Newby | 356/244 |
| 3,777,283 A | 12/1973 | Elkins | |
| 4,111,754 A | 9/1978 | Park | |
| 4,501,496 A | 2/1985 | Griffin | |
| 4,607,921 A | 8/1986 | Miller | |
| 4,731,335 A | 3/1988 | Brigati | |
| 4,790,640 A | 12/1988 | Nason | |
| 4,849,340 A | 7/1989 | Oberhardt | |
| 4,985,206 A | 1/1991 | Bowman et al. | |
| 5,605,813 A | 2/1997 | Stevens et al. | |
| 5,618,731 A * | 4/1997 | Stevens et al. | 435/304.3 |
| 6,118,582 A | 9/2000 | Del Buono | |
| 6,485,690 B1 * | 11/2002 | Pfost et al. | 422/102 |
| 6,508,988 B1 * | 1/2003 | Van Dam et al. | 422/102 |

FOREIGN PATENT DOCUMENTS

| | | |
|---|---|---|
| CN | 12901950 A | 4/2001 |
| EP | 0047189 A1 | 3/1982 |
| EP | 0310399 A2 | 4/1989 |
| EP | 0479231 B1 | 3/1996 |
| GB | 2 127 577 A | 4/1984 |
| JP | 49-34827 Y1 | 9/1974 |

(Continued)

OTHER PUBLICATIONS

Canadia Office Action, dated Mar. 1, 2011.

(Continued)

*Primary Examiner* — Jill Warden
*Assistant Examiner* — Dwayne K Handy
(74) *Attorney, Agent, or Firm* — Sughrue Mion, PLLC

(57) ABSTRACT

A cover for a substrate including: a body defining a cavity, for positioning over the substrate to form a reaction chamber; and a projection extending from the body to define a fluid reservoir, when the cover is fitted to the substrate, the fluid reservoir being in fluid communication with the cavity.

25 Claims, 15 Drawing Sheets

FOREIGN PATENT DOCUMENTS

| | | |
|---|---|---|
| JP | 63-019532 | 1/1988 |
| JP | 3-40545 U | 4/1991 |
| JP | 4-214519 A | 8/1992 |
| JP | 7-113731 A | 5/1995 |
| JP | 8-334702 A | 12/1996 |
| JP | 9-236756 A | 9/1997 |
| JP | 2000-508423 A | 7/2000 |
| WO | 85/04719 A1 | 10/1985 |
| WO | WO 97/39328 A1 | 10/1997 |

OTHER PUBLICATIONS

European Search Report Appln. S.N.: 03729709.0-1270; Mar. 16, 2011.

Notification of Reasons for Refusal of corresponding Japanese Application No. 2004-514434 dated Jan. 8, 2008.

Notification of Reasons for Refusal of corresponding Japanese Application No. 2004-514434 dated Sep. 1, 2009.

* cited by examiner

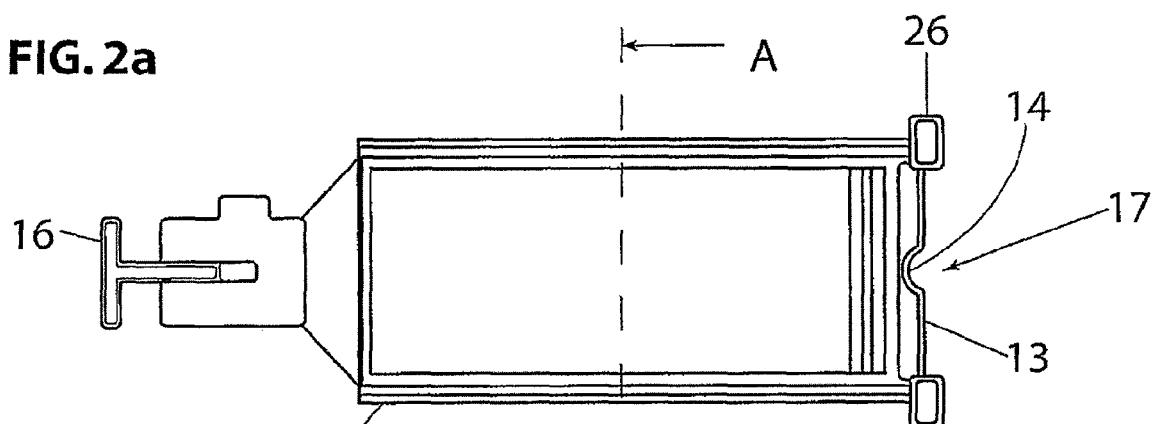
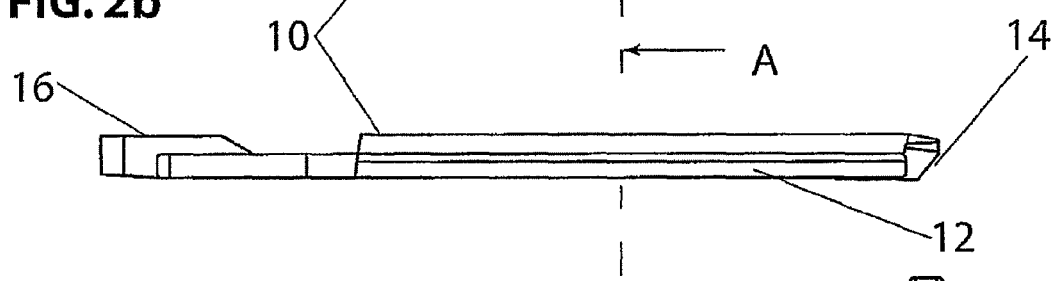
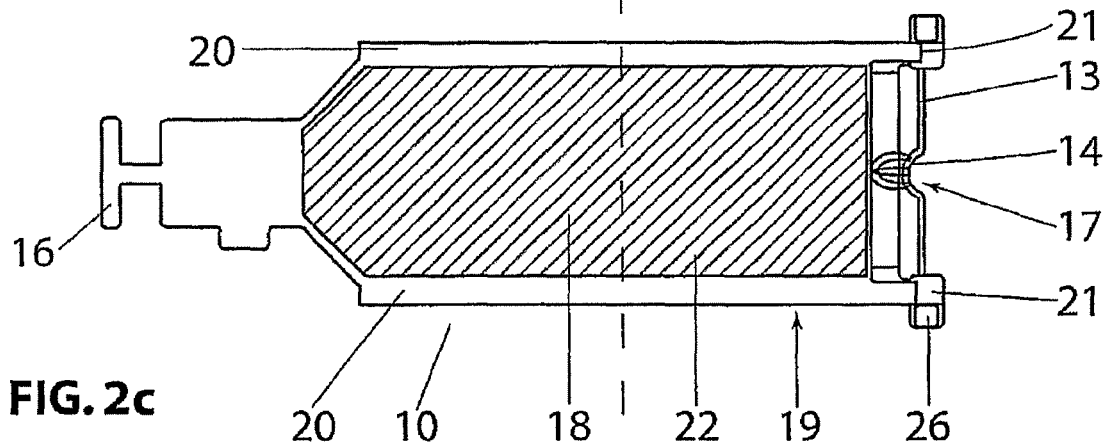

SECTION A-A

Top View

Bottom View

MICROSCOPE SLIDE COVER WITH INTEGRATED RESERVOIR

CROSS-REFERENCE TO RELATED APPLICATION

This application is a divisional of application Ser. No. 10/518,478, filed Jul. 26, 2005, which is a 371 of PCT Application No. PCT/AU2003/000778 filed Jun. 20, 2003, which claims priority from Australian Patent Application No. PS3090/02 filed Jun. 20, 2002, which applications are incorporated herein by references.

FIELD OF THE INVENTION

The present invention relates to a cover for a substrate, and in one form a cover for use with a microscope slide.

BACKGROUND OF THE INVENTION

Microscope slides are commonly used to view samples of material under a microscope. The samples may contain human tissue, and may require treatment such as staining, so that properties of the sample can be identified. Other materials such as DNA, RNA, or proteins may be included on the slide.

It is common for several reactions to be undertaken on a sample on a slide. Once the reactions have taken place the slide may be viewed under a microscope. Performing the reactions on the slide can be difficult to automate, as the tissue samples require careful preparation and certain reactions require carefully controlled environments.

SUMMARY OF THE PRESENT INVENTION

In accordance with the present invention, there is provided a cover for a substrate including:
a body defining a cavity, for positioning over the substrate to form a reaction chamber; and
a projection extending from the body to define a fluid reservoir, when the cover is fitted to the substrate, the fluid reservoir being in fluid communication with the cavity.

Preferably the cavity extends the full width of a sample holding region on the substrate.

Preferably, a protrusion extends from the projection, to assist in wicking fluid into the reservoir.

Preferably, the reservoir is defined between the projection, which is spaced from the substrate, and legs located at sides edge of the cover.

In one form the projection is formed from two sections, the first section is angled at least at substantially 60° relative to the cavity and the second section is angled at least at substantially 15°.

In one form, the cover further includes a second reservoir, at an opposite end of the cover.

Preferably wall portions are located at the edge of the cover, surrounding the cavity on two or more sides.

In one form the legs extend along the sides of the cover to form the wall portions.

In a preferred form, the cover includes a locator for controlling and locating the cover, the locator being arranged at an end of the cover opposite the projection.

In one form the cavity extends to an end edge of the cover adjacent the locator.

In one form the cover is supported on the substrate by the wall portions.

Preferably, the cover is made from a polymer material.

In one form the cavity includes a coating of reduced surface roughness than the polymer material.

In another form the cavity includes a coating with reduced porosity.

In another form the cavity has one or more coatings.

Preferably a first coating is a material having similar properties to the material of the slide.

Preferably the first coating is silicon dioxide.

Preferably a second coating is placed intermediate a first coating to provide improved contact properties between the cover and first coating.

Preferably, the cover has associated wing structures that allow the cover to be engaged and pivoted relative to the substrate so as to open the reaction chamber and allow the slide to be cleared of fluid.

In another aspect, there is provided a combination of a substrate and a cover, as described above, wherein the cavity of the cover is arranged to face the substrate so as to form a reaction chamber.

In yet another aspect, there is provided a method of treatment of a sample on a sample holding region of a substrate, including locating a cover, as described above, over the substrate, so that the cavity of the cover faces the substrate to form a reaction chamber over the sample holding region, and depositing fluid into the fluid reservoir to allow the fluid to be drawn into the reaction chamber, as required.

Preferably, the method further includes sliding the cover relative to the substrate to vary a degree of overlap between the cover and the sample holding region, which results in a corresponding variation in the reaction chamber volume.

Preferably, the method further includes sliding the cover relative to the substrate until wing structures associated with the cover are engaged and lifted relative to the substrate to pivot the cover into an open condition, and allow fluid to drain from the reaction chamber.

BRIEF DESCRIPTION OF THE DRAWINGS

The invention is described, by way of non-limiting example only, with reference to the accompanying drawings, in which:

FIGS. 2 (*a*)-(*c*) show top, side and bottom views of a first example of a cover for a slide;

DETAILED DESCRIPTION

Figure 1:
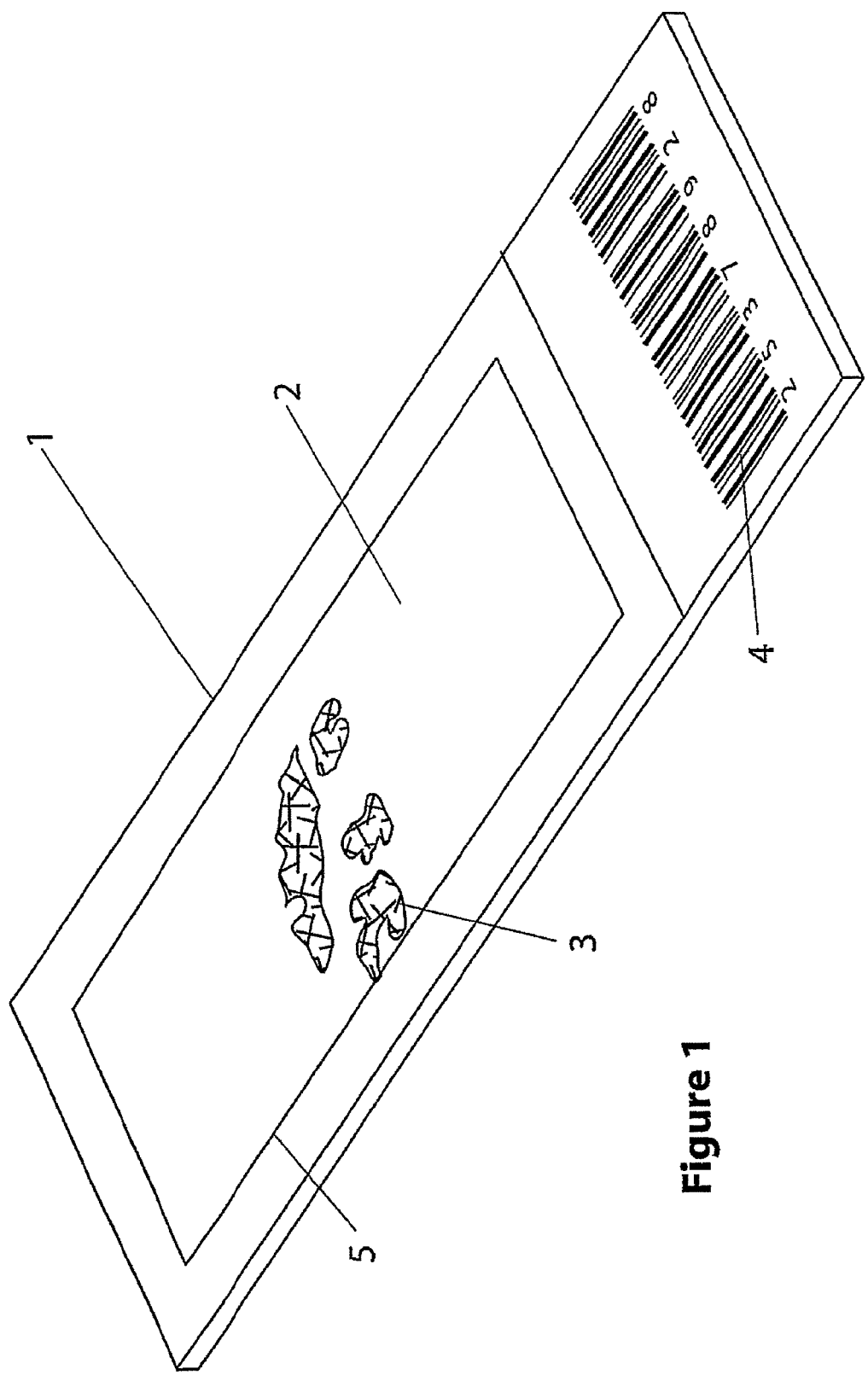
FIG. 1 shows an example of a microscope slide.

A microscope slide 1 is shown in FIG. 1 as including an upper surface 2 containing a sample 3. The slide 1 is identified by a unique bar code 4. The sample 3, such as a thinly sliced tissue section, is located on the slide 1 in a sample holding region 5, which needs to be covered by a cover, such as shown in FIG. 2, for subsequent application of test fluids and the like.

Figure 3:
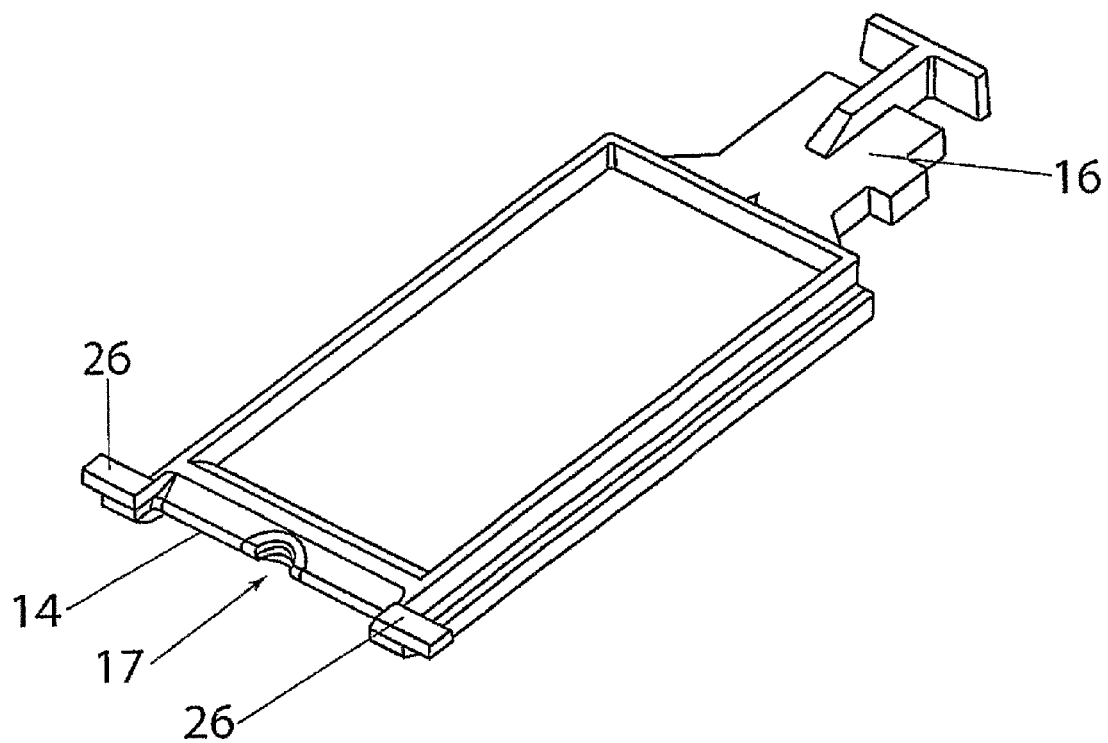
FIG. 3 shows a perspective view of the cover of FIG. 2.

FIGS. 2 (a)-(c) and FIG. 3 show a cover 10 as having a body 12, a fluid receiving zone 14, a locating means 16 and a cavity 18 on an underside face 19. Surrounding the cavity 18 on two sides is a wall portion 20. At one end of the cover 10, the wall portion 20 joins with legs 21 which extend upwardly and away from the face 19. The legs 21 are spanned by a projection 13 which defines a fluid reservoir 17, between an underside of the projection and the legs 21.

Figure 4A:
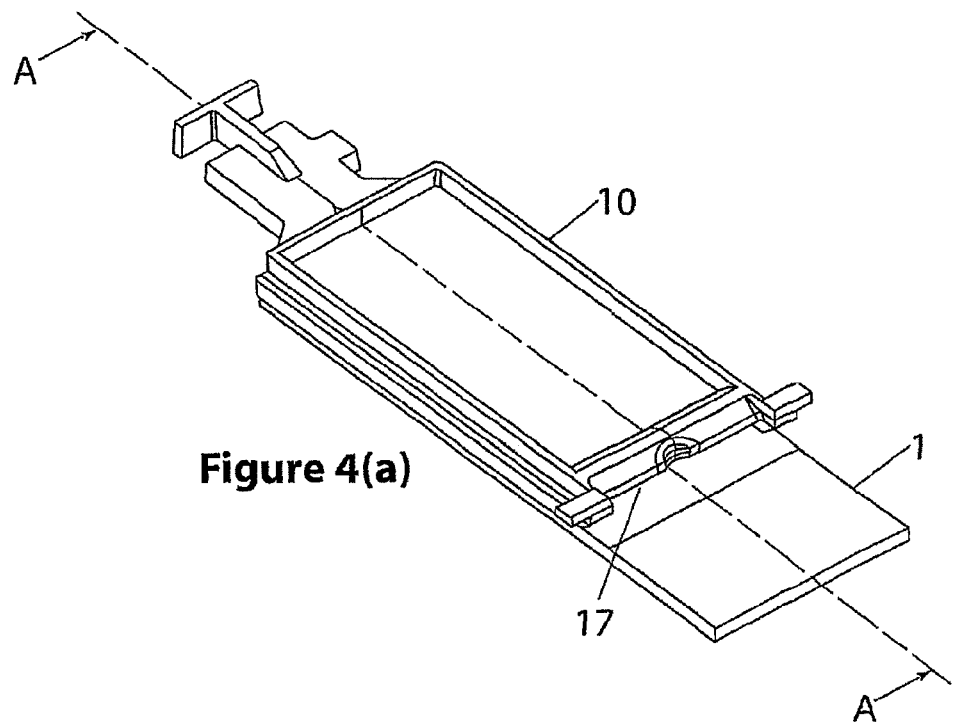
FIGS. 4 (*a*)-(*c*) show further views of the cover of FIG. 2 located on the slide of FIG. 1.
Figure 4B:
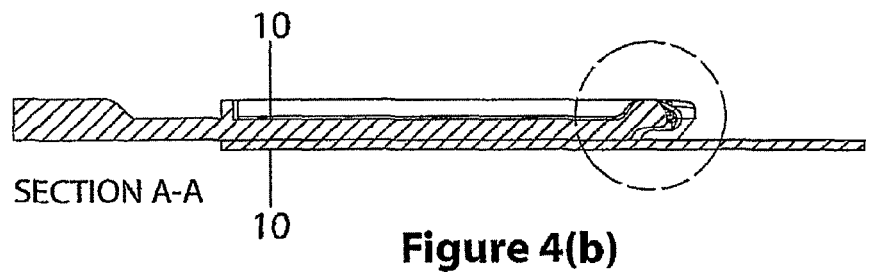
Figure 4C:
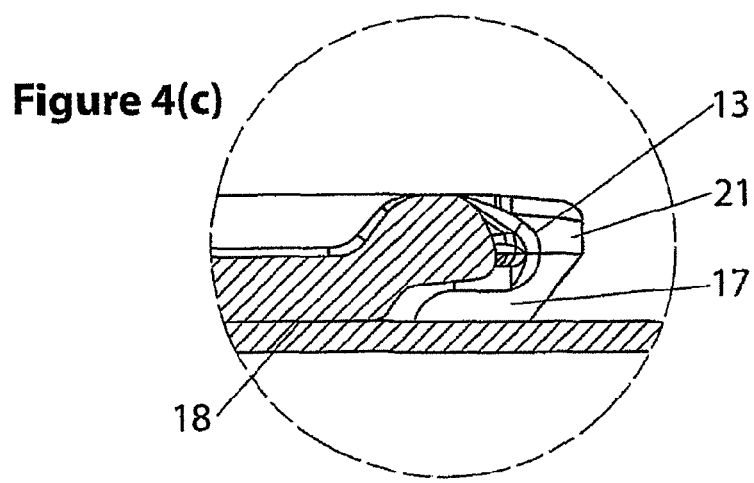
Figure 5:
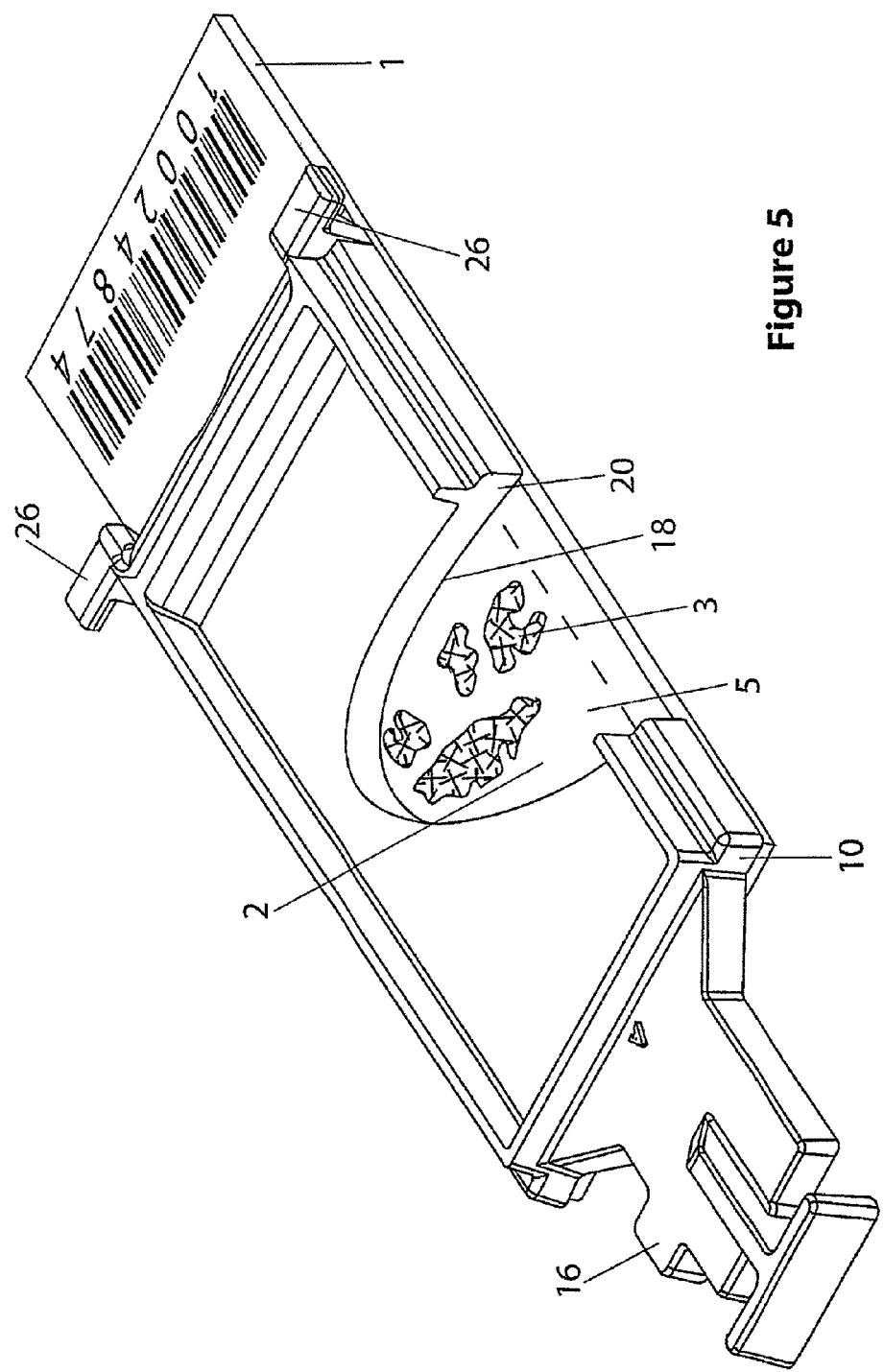
FIG. 5 is a perspective view of the cover and slide arrangement of FIG. 4, showing a cutaway section of the cover.

The cover 10 is shown fitted to a slide 1 in FIGS. 4 and 5. The fluid reservoir 17 is shown most clearly in FIG. 4 (c) where a detailed view of part of a section A-A taken across the cover 10 and slide 1 is illustrated. The projection 13, with leg 21 at either end, is raised relative to the slide 1, to form a volume capable of holding fluid dispensed onto the slide 1. In this way fluid reservoir 17 enables fluid dispensed onto slide 1 to be held until required, without spilling off an edge of the slide. The projection 13 further assists in spreading the fluid across the full width of the cavity 18.

Figure 6:
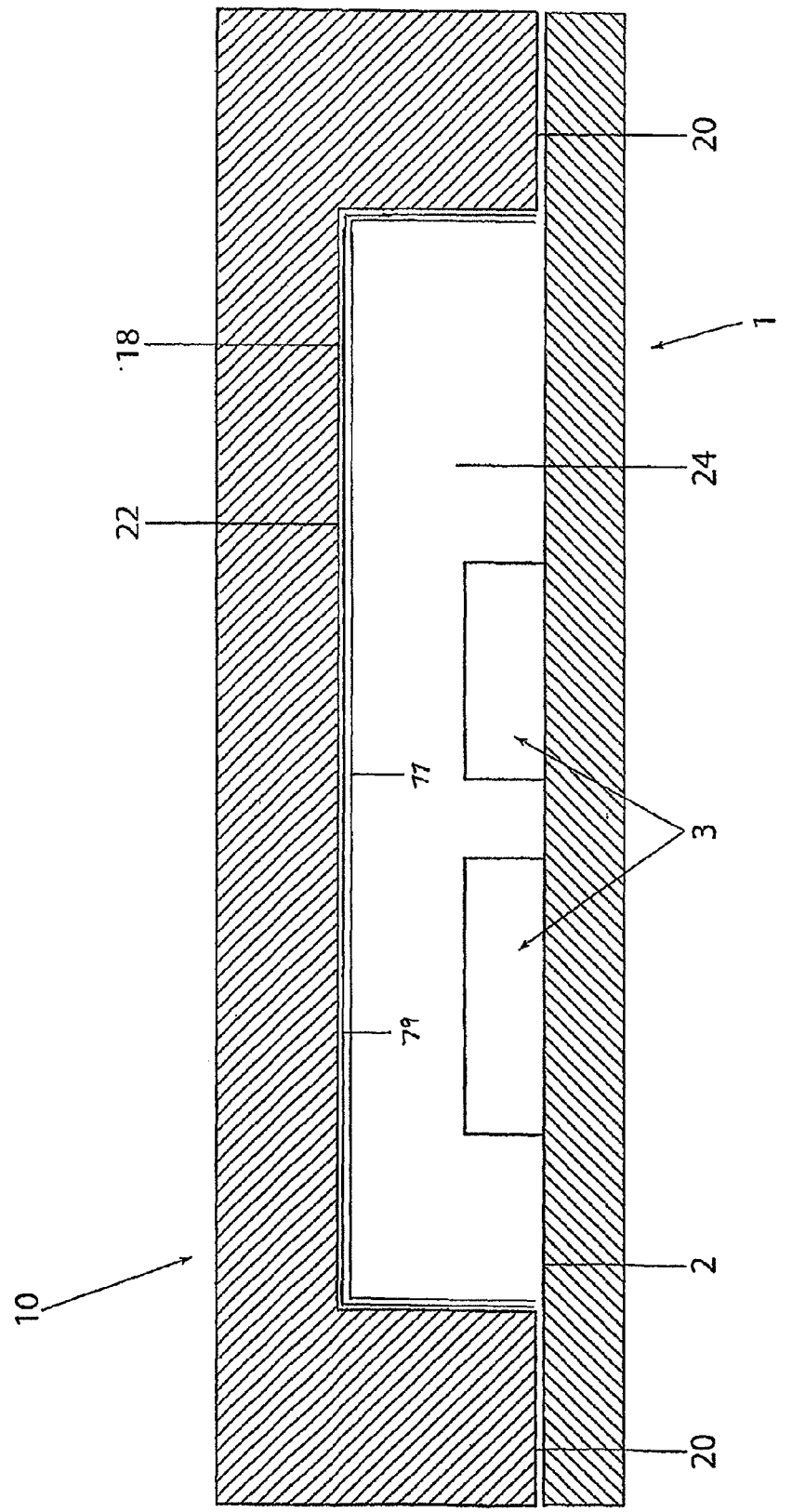
FIG. 6 shows a schematic cross section of the cover and slide of FIG. 5.

The overlap of the cavity 18 with the slide 1 forms what may be described as a reaction chamber, as illustrated in FIG. 6. The cavity may vary according to application, typically from 20-200 microns. The wall portion 20 is adapted to support the cover on the slide 1. The cavityed face 22, wall portion 20 and sample holding region 5 of a slide 1 form a reaction chamber 24 when the cover 10 is placed at least partially over the sample holding region 5.

The fluid reservoir 17 is typically sized to be larger than the volume of the reaction chamber 24, for example 150% of the volume of the reaction chamber. This provides sufficient volume of fluid to fill the reaction chamber completely, while allowing some excess to flush the chamber, and an amount to be retained in the fluid reservoir to provide a reservoir for evaporation.

Clamping forces may also be applied to the cover once loaded onto the slide, and these forces are designed to provide a seal between the wall portions 20 and the upper surface of the slide 1. This is to restrict fluid leakage from the side of the cover. In one example (not shown) the wall portions may have an additional member to assist sealing of the wall portions with the upper surface 2 of the slide 1. This additional member may be a softer polymer or rubber material.

Figure 18:
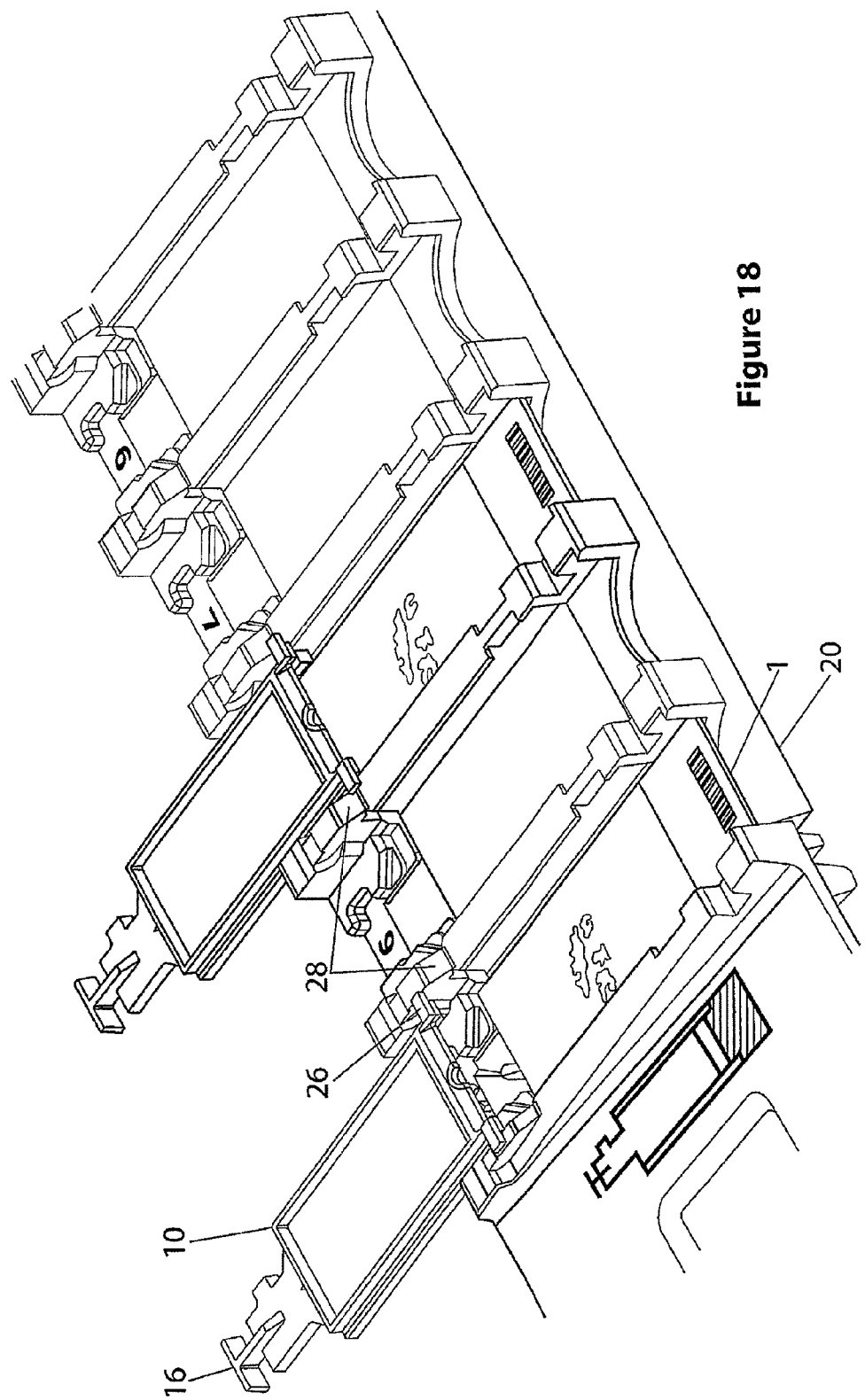
FIG. 18 shows the cover of FIG. 2 mounted to the tray of FIG. 7.
Figure 19A:
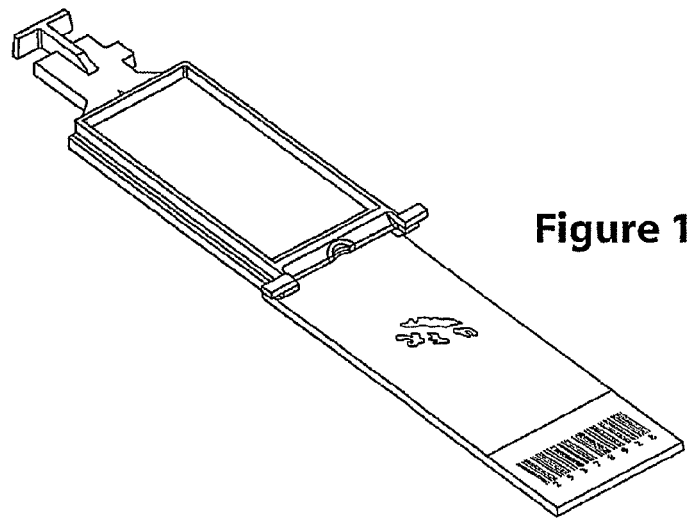
FIGS. 19 (a)-(c) shows the cover of FIG. 2 in various positions over the slide of FIG. 1.
Figure 19B:
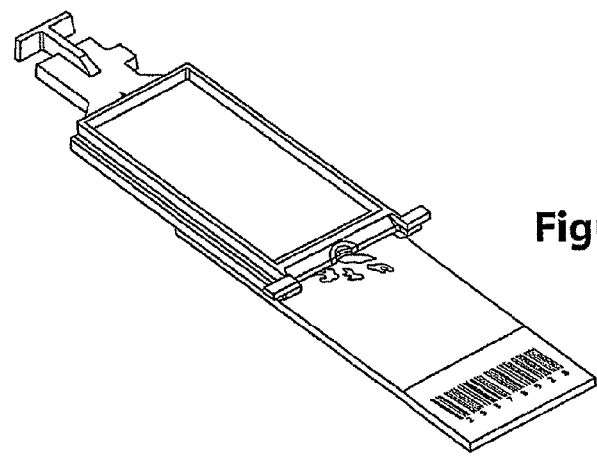
Figure 19C:
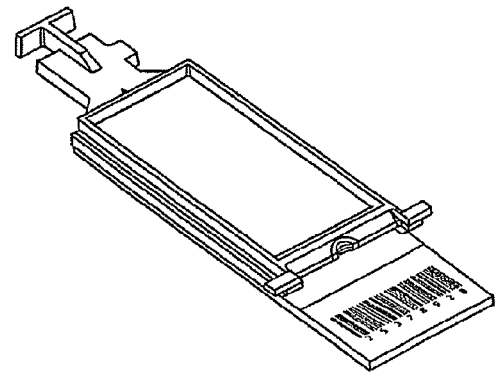

The cover 10 also includes engaging surfaces in the form of wings 26. The wings 26 are adapted to engage ramps 28 of a tray 21 shown in FIG. 7, to thereby lift the cover clear of the surface of the slide 1. An example of the wings lifting the cover free is shown more clearly in FIG. 18. The cover 10 may be controlled by an arm (not shown) moving the locating means 16. The cover 10 may be placed in a number of positions over the slide, exemplified by the positions of the cover relative to the slide shown in FIG. 19. In FIG. 19(a), the cover 10 is in an open position relative to the slide 1, as the sample is exposed and open. FIG. 19 (b) shows the cover in a partially closed position, and FIG. 19 (c) shows the cover in a fully closed position, where the sample is completely covered by the cover and is therefore wholly contained within the reaction chamber 24. The reaction chamber formed by the cover and cavity 18, as shown in FIG. 5, extends over most of the slide 1. However it is possible that the sample may be placed more towards the end of the slide distal from the bar code 4, and therefore a smaller reaction chamber 24 is required. Reducing the size of the reaction chamber 24 reduces the amount of fluid required to fill the chamber, which can be important where expensive or scarce fluids are used. It is possible to form a smaller reaction chamber with the cover 10, by only covering a portion of the slide 1 with the cover 10. This position is shown in FIG. 19 (b).

Variations in cover constructions are schematically shown in FIGS. 8-17. In FIGS. 8-17, only the front segments of the covers are shown, and the locating means 16 have been omitted from view for clarity and like parts are denoted by like reference numerals.

Figure 8A:
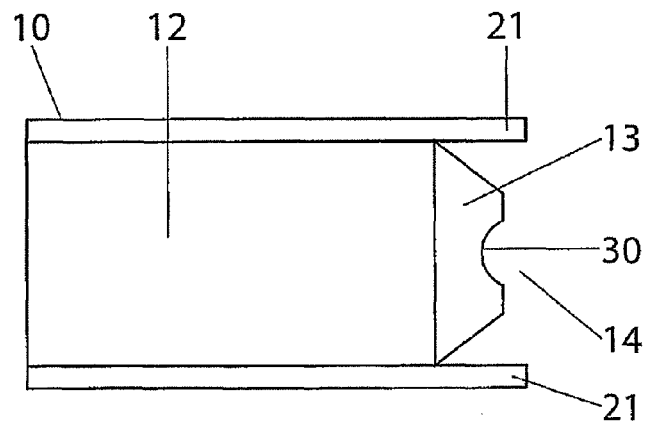
FIGS. 8 (*a*) and (*b*) show schematic top and sectional side views, respectively, of a further example of a cover.
Figure 8B:
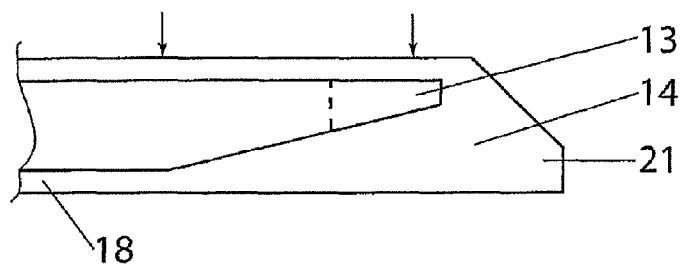
Figure 9A:
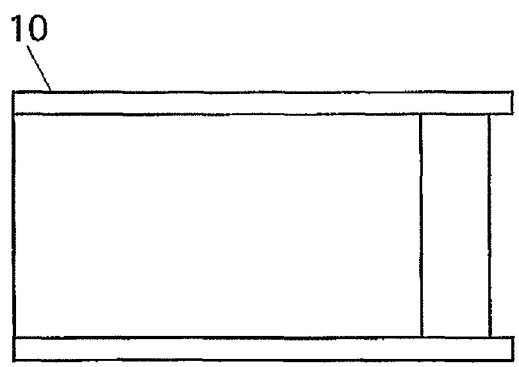
FIGS. 9 (*a*) and (*b*) show schematic top and sectional side views, respectively, of a further example of a cover.
Figure 9B:
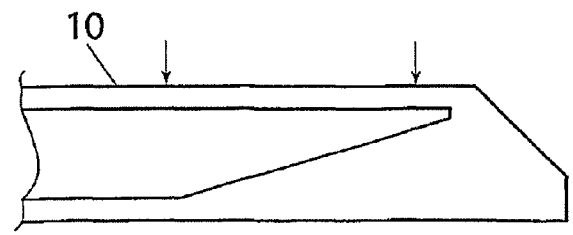

In FIG. 8(a) a cover 10 is shown having a body 12, projecting legs 21, a protruding section 13 and an indent 30. The projecting legs 21 either side of the body 12 form a fluid receiving zone 14. When placed onto a slide, fluid may be dispensed into the fluid receiving zone, where it spreads in a circular fashion to contact the protruding section 13. The indent 30 allows the fluid to contact a wider portion of the protruding section 13 than if the front edge of the protruding section was straight (as shown in FIG. 9). Once the fluid is in contact with the protruding section 13, it wicks across the width of the cavity 18. If suction is applied at the rear of the cavity, or the cover is moved along the slide from an open position to a more closed position, then the fluid begins to fill the cavity 18. When the cavity 18 has moved across the sample 3, it forms the reaction chamber 24 as the fluid may react with the sample 3.

FIGS. 9 (a) and (b) show a more simple construction of a cover 10 that may be used in some circumstances. The operation of the cover 10 is the same as the operation of the cover 10 in FIGS. 8 (a) and (b).

Figure 10A:
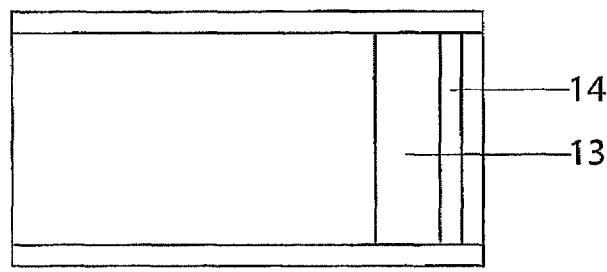
FIGS. 10 (*a*) and (*b*) show schematic top and sectional side views, respectively, of a further example of a cover.
Figure 10B:
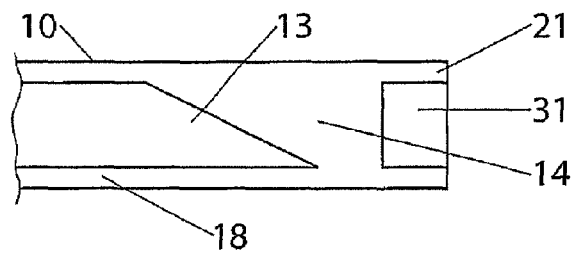

FIGS. 10 (a) and (b) show a cover 10 having a body 12 with projecting legs 21. A protruding section 13 and a bar 31 surround a fluid receiving zone 14 for receiving fluid. The fluid may be dispensed onto the protruding section 13, where it flows down and onto the slide surface 2. The protrusion 13 and bar 31 cause the fluid to spread across the width of the cavity 18, enabling the cavity to be filled with fluid.

Figure 11A:
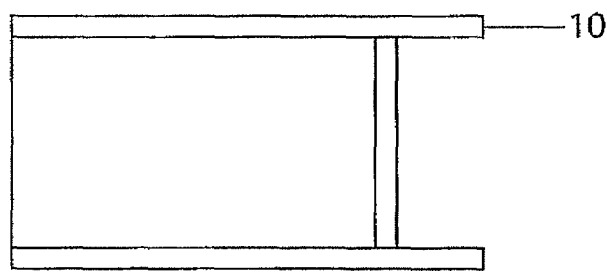
FIGS. 11 (*a*) and (*b*) show schematic top and sectional side views, respectively, of a further example of a cover.
Figure 11B:
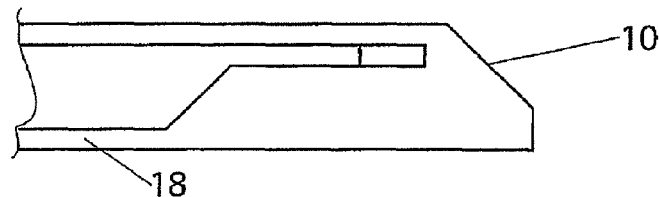
Figure 12A:
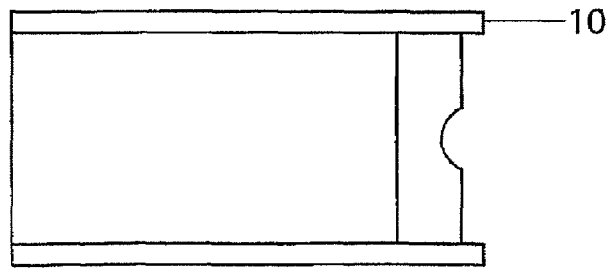
FIGS. 12 (*a*) and (*b*) show schematic top and sectional side views, respectively, of a further example of a cover.
Figure 12B:
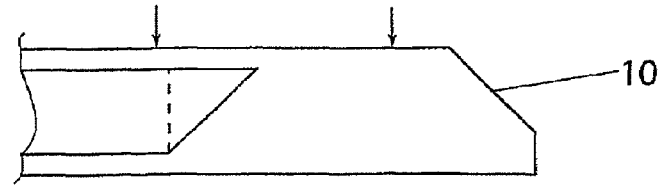
Figure 16A:
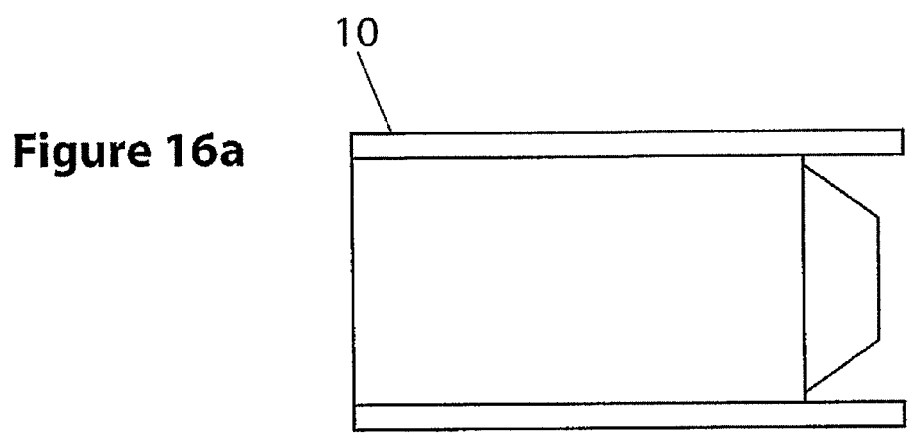
FIGS. 16 (a) and (b) show schematic top and sectional side views, respectively, of a further example of a cover.
Figure 16B:
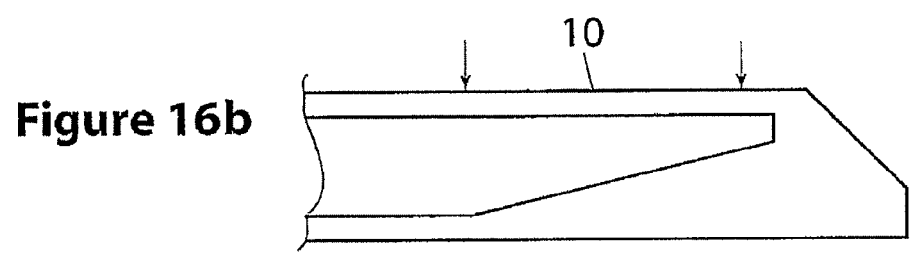

The covers 10 of FIGS. 11, 12 and 16 operate in similar ways to those described above.

In relation to all of the above-described covers, it should be appreciated that the covers are generally 25 mm across, and the cavity 18 is typically only 20-200 micrometres high. As such, overall fluid dispense volumes may be in the order of 20-300 microlitres.

Figure 13A:
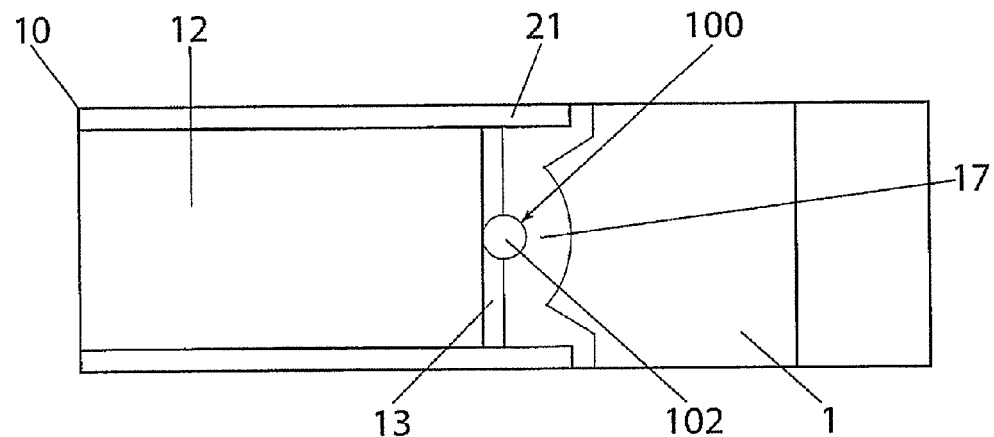
FIGS. 13 (*a*) and (*b*) shows schematic top and sectional side views, respectively, of a further example of a cover.
Figure 13B:
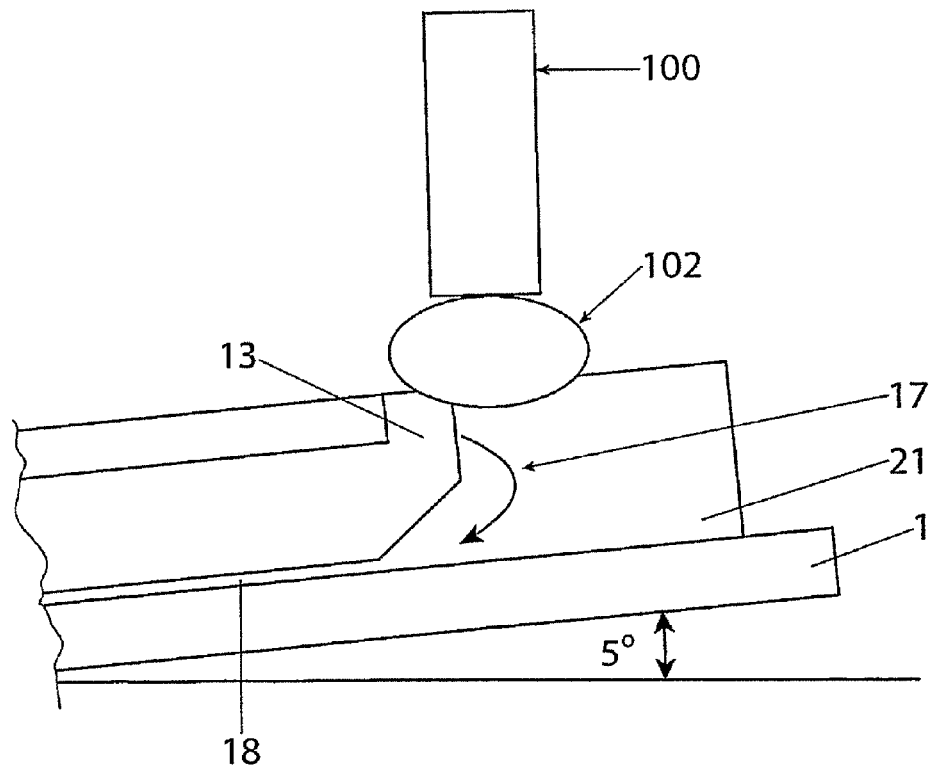

FIG. 13 (a) shows another cover 10 having a body 12, legs 21 and a fluid dispenser 100 dispensing fluid 102 onto the slide 1. In FIG. 13 (a), the fluid 102 has already been dispensed, and has formed a fluid reservoir in the fluid reservoir 17. The schematic Figure shows a typical wicking pattern formed by the fluid as it contacts the cover 1. In FIG. 13 (b), the fluid is just being dispensed onto the projection 13. In the volumes dispensed, the fluid forms a pool of comparable size to some of the cover features. Not only does the fluid flow forward of the cover as shown in FIG. 13 (*a*), but it also flows under the cover to at least partially fill cavity 18. As mentioned above the fluid may be drawn into the cavity further by movement of the cover over the slide or suction applied to the rear of the cavity 18.

Figure 14A:
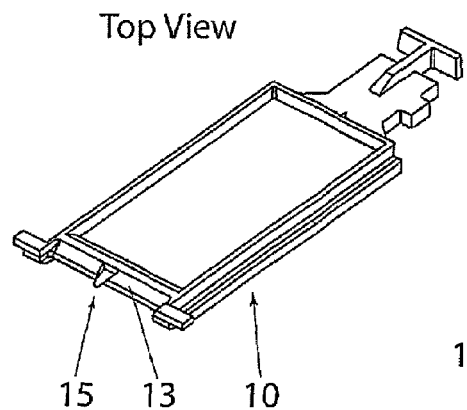
FIGS. 14 (*a*) and (*b*) show top and bottom perspective views, respectively, of a further example of a cover.
Figure 14B:
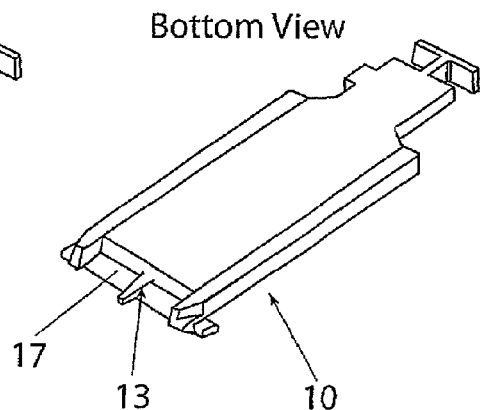
Figure 15:
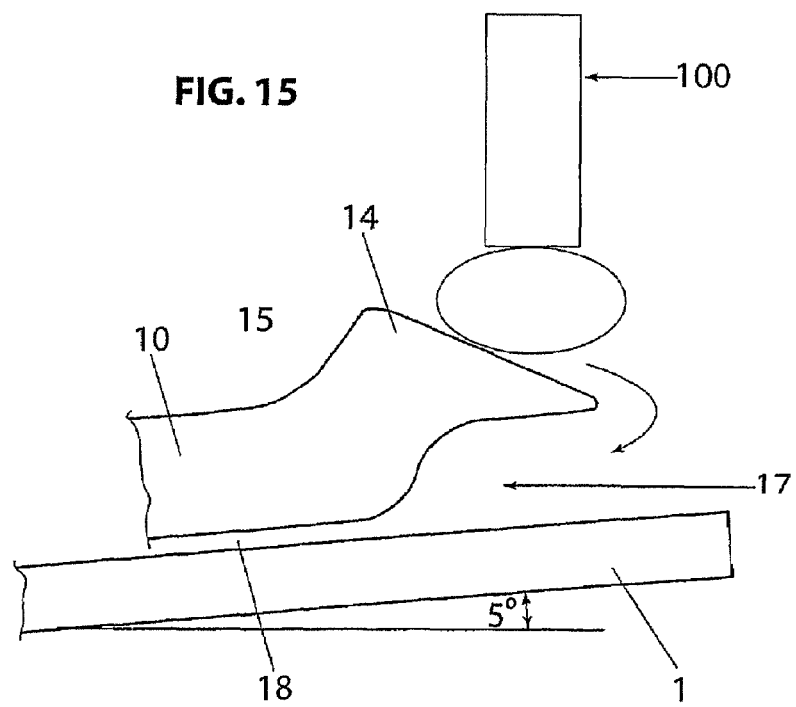
FIG. 15 shows a schematic side view of a nose portion of a cover.

FIGS. 14 (*a*) and (*b*) shows a further embodiment of a cover 10 where like reference numerals are again used to denote like ports. The cover has a fluid reservoir 17, a projection 13, and a protrusion in the form of nib 15. Fluid may be deposited directly on the nib 15 so that the fluid rolls over the projection 13 into reservoir 14, and to the cavity 18, as required. If fluid is placed too far ahead of the cover, there are circumstances that may cause the fluid to reach the edge of the slide before wicking across the width of the cavity 18. It has been found that using the projection 13 causes the dispensed fluid to contact the covertile and spread along the full width of the cavity 13, due to the positive attraction of the covertile and the fluid. The capillary forces in the cavity cause the fluid to spread out, and the reservoir holds sufficient fluid to ensure that fluid dispensed onto the slide at least fills the cavity 18. The nib 15 is useful in that if the pipette is not placed to dispense the fluid accurately onto the slide, and for example misses a few millimetres in front of the projection, the nib 15 will be likely to contact the fluid, which will be drawn to the protrusion and into the reservoir. This assists in reducing bubble or void formation within the cavity. The nib 15 may extend approximately 1-5 mm from the projection 13.

Figure 17:
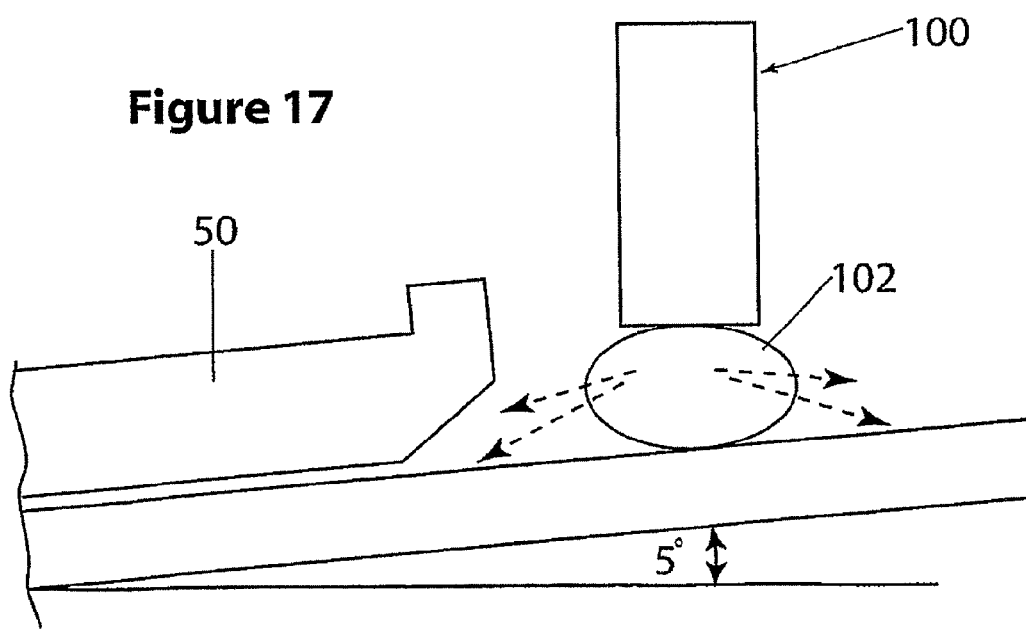
FIG. 17 shows a schematic side view of a further example of a nose portion of a cover.

FIG. 17 shows an example of how fluid spreads across a slide when deposited in front of a cover 50. A variety of profiles for the underside of a projection 15 may be employed.

Figure 7:
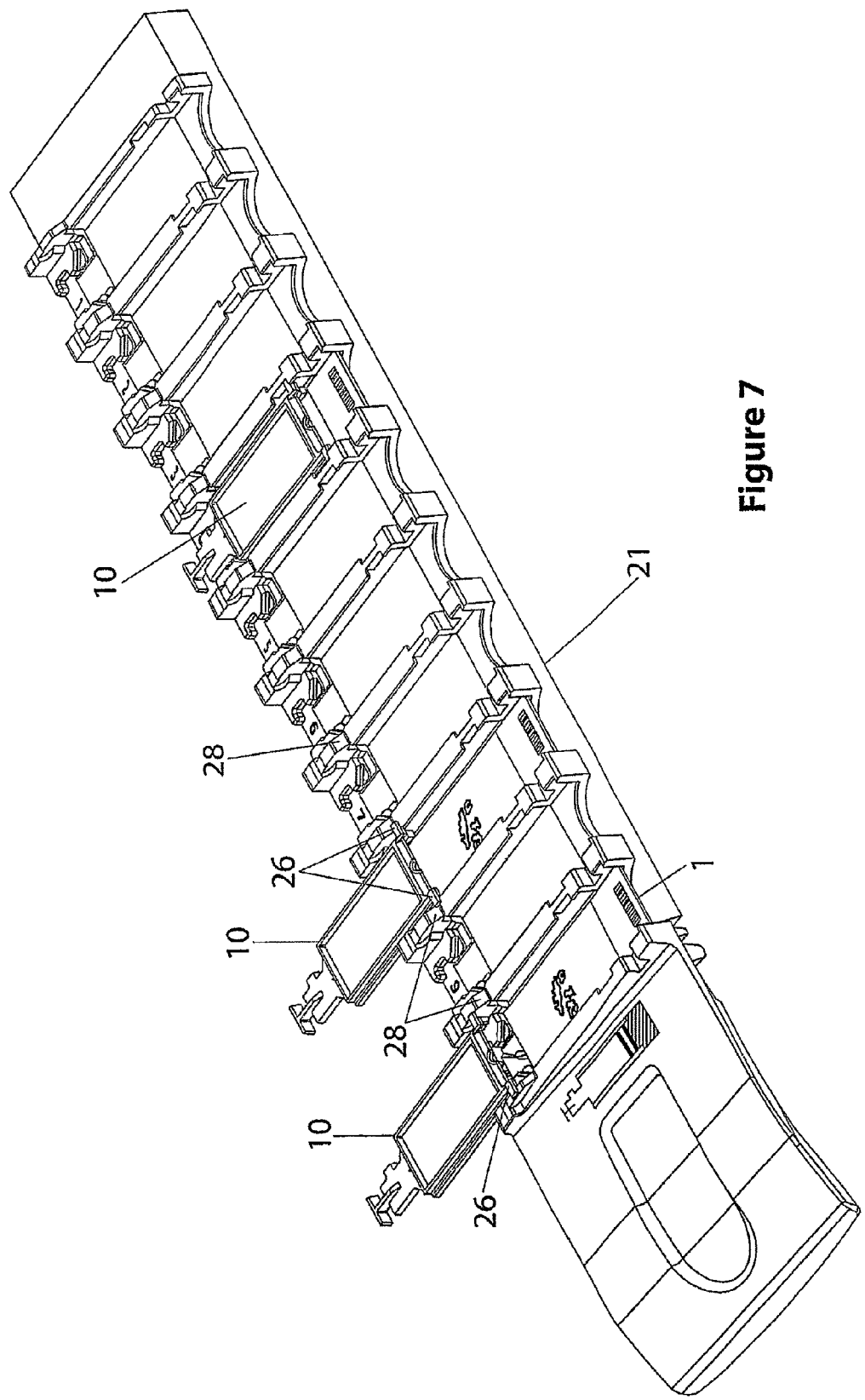
FIG. 7 shows a perspective view of a tray adapted to locate covers and slides.

In use, a cover 10 is placed on a slide 1, as shown in FIGS. 4, 5 and 6 to cover the sample 3. The slide 1 will typically be in a tray 21 as shown in FIG. 7, said tray 21 able to hold, for example, 10 slides and covers of the examples shown. The tray 21 may then be placed into a biological reaction apparatus, such as that disclosed in Australian Provisional Patent Application No. PS3114/02 by the same applicant, titled "Method and Apparatus for Providing a Reaction Chamber", filed 20 Jun. 2002, and its associated international patent application, filed 20 Jun. 2003, the contents of which are hereby incorporated by reference.

Once the tray 21 is loaded into the apparatus (not shown) the slides 1 are held in position, typically at an angle of 5 degrees to the horizontal as shown schematically in FIG. 13 (*b*), 15 or 17. The cover 10 is then moved by an arm (not shown) engaging the locating means 16. Typically, during a sequence referred to as an "open fill", the cover 10 is moved longitudinally along the surface of the slide 1 until the sample 3 is exposed. A fluid is then dispensed by a dispensing means 100 such as a probe attached to a pump, onto the fluid receiving zone 13 (as shown in FIG. 13 (*b*)). The amount of fluid dispensed is typically sufficient to fill the reaction chamber 24. The use of the cover 10 with this fill mechanism or methodology allows a small volume of fluid to be uniformly distributed across the reaction chamber 24. Distributing the fluid across the reaction chamber 24 evenly and without bubbles or air spaces allows reactions to take place on the sample 3 with greater consistency. Also, dispensing fluid into an empty receiving zone where the reaction chamber already contains fluid causes the fluid within the chamber to be replaced by the fluid in the receiving zone minimising mixing of the fluid in the reaction chamber and newly dispensed fluid. The dimensions of the reaction provide a smooth flow of fluid from the reaction chamber such that there is little mixing of the fluids. This is advantageous as it allows a previous fluid to be replaced accurately, with minimal original fluid remaining to contaminate later fluids or reactions. This reduces the number of washes required to clear the reaction chamber 24.

The volume of fluid in a reaction chamber 24 may be, for example 150 microlitres or less, although volumes may vary depending on the application and the reaction chamber dimensions.

The reaction chamber 24 is able to retain fluid due to the surface tension of the fluid, unless additional fluid is added to the fluid receiving zone, or suction is applied (typically through reduced air pressure) at the end of the slide opposite the fluid receiving zone. The reaction chamber may be filled as it is formed by the cover 10 being moved along the surface of the slide 1 to cover the sample holding region 52. Alternatively, the reaction chamber may be filled without the cover being moved relative to the slide, due to the process of capillary wicking of dispensed fluid into the reaction chamber.

In the present examples the cover may be clamped to the slide when not in motion or retracted for an initial fill. The clamping mechanism (not shown) places force around the edge of, for example, cover 10 adjacent the wall portions 20 to locate the cover 10 with respect to the slide 1 during a reaction.

During the withdrawal of the cover 10 from the slide 1 it is sometimes desirable to remove the cover from contact with the slide. In order to accomplish this, wings 26 engage the ramps 28 to lift the cover clear of the slide. This causes the cover 10 to lift off the slide 1 to prevent fluid contact between the slide 1 and cover 10. In this way the slide can be cleared of virtually all fluid.

Parts of the cover may have different material properties compared to the properties of the material of the cover body 12, which is typically plastic. In one example (not shown) the cavity may have different material properties, in order to provide a reaction chamber 24 with certain material properties. A clear plastic material has been found to be suitable for the body 12 of the cover 10, to provide suitable mechanical properties such as reasonable strength and rigidity. The cover needs to be sufficiently strong to be moved while clamping forces are applied to the cover, as the clamping forces assist in providing a sealing surface between the walls 20 of the cover 10 and the upper surface of the slide 1. The cover may be moved to empty or fill the chamber, or also, to promote fluid movement within the reaction chamber to assist a reaction.

The cover should ideally have some flexibility, as it is desirable that upon application of the clamp, the cavityed face should deflect somewhat. This has been found to assist in moving the fluid within the reaction chamber and therefore increases the exposure of the sample to the fluid.

Other properties of the cover 10 include the ability to restrict the heat loss from the surface of the slide 1. Typically the slide will be mounted on a heated block, and the cover will be placed over the sample on the slide. Heating the slide heats the sample and the fluid in the reaction chamber. If there is excessive heat loss from the cover 10 it is difficult to regulate the temperature of the fluid by heating the slide 1. Further, there may be an excessive temperature gradient across the reaction chamber 24, which is undesirable.

The cavityed face 19, as shown in FIG. 2, may have different surface properties to the rest of the cover. It has been found to be desirable to have similar material properties for the upper surface of the slide 2 and the cavity 18. In one example, it is possible to coat the surface of the cavity with a material 77 (shown in FIG. 6), such as silicon dioxide. This coating may be approximately 110 nm thick. The coating provides a surface with material properties similar to that of a glass slide. It has also been found that there are benefits in applying a thin layer 79 (for example 0.5-6 nm) of Chromium Oxide (Cr2O3) to the cavity before applying the silicon dioxide layer. This application of an intermediate layer between the silicon dioxide and plastic provides better adhesion and better thermal expansion properties for the cavity. Further, coatings in general may be used to improve the flatness of the cavity (which reduce nucleation sites and therefore bubble formation at high temperatures). The coatings may be used to modify the capillary flow characteristics of the fluid within the reaction chamber, create an impermeable barrier for gas or liquid between the cover and fluid in the reaction chamber, or provide a chemically inert surface.

In another example, it is possible to replace the cavityed face 19 with a glass insert supported by the plastic body 12 of the cover 10. It may also be possible to change the surface properties of the plastic by plasma discharge.

The covers shown in the examples may be used at temperatures approaching 100 degrees Celsius, especially when used for in-situ hybridisation reactions. At higher temperatures, the fluid evaporates and bubbles are produced. The heating may also cause the cover to bow—the cavity surface is hotter than the top of the cover and expands more, causing the cavity surface to 'sag' towards the slide. This helps to remove the bubbles, as the fluid wants to occupy the smaller spaces more than the bubbles do. The bubbles congregate at the ends of the cavity, and must be allowed to escape.

Figure 20A:
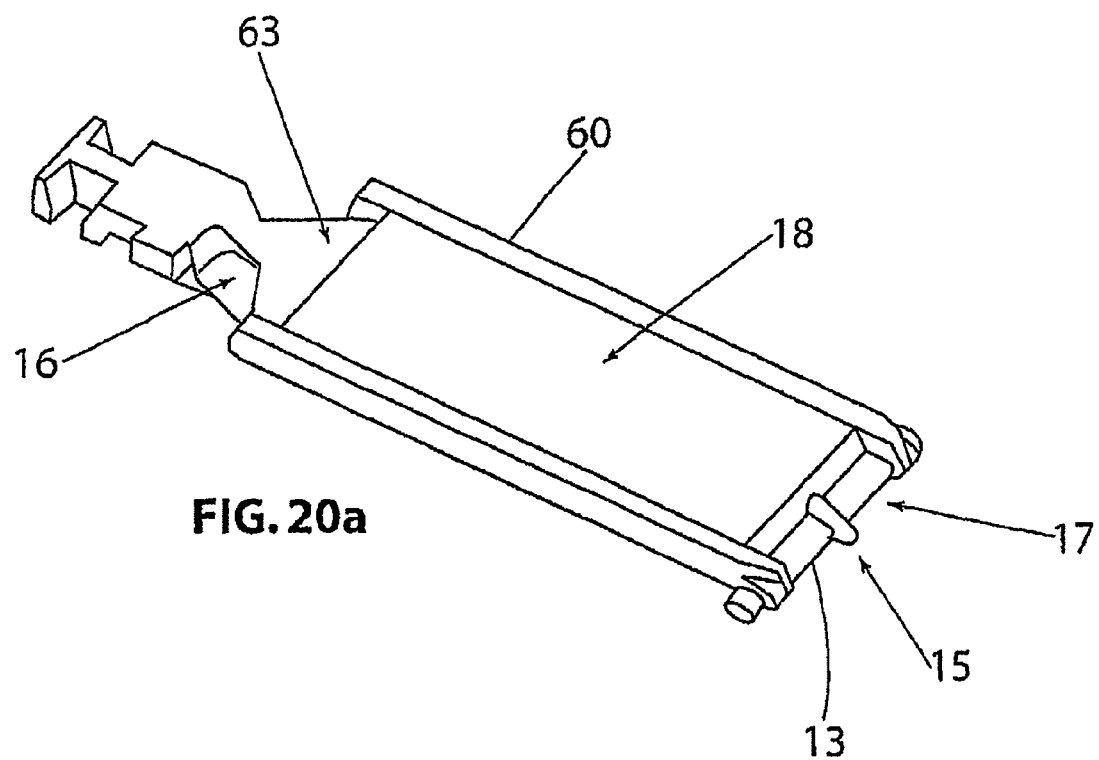
FIGS. 20(a) and (b) show a bottom perspective view and enlarged partial perspective view, respectively of a modified cover.
Figure 20B:
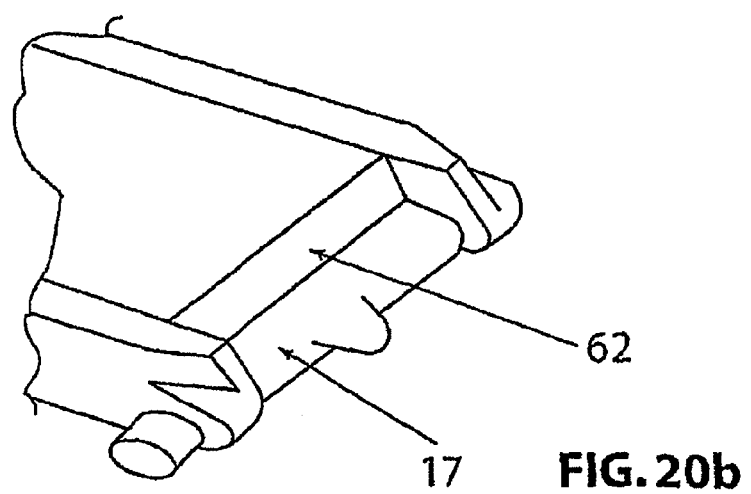

Experiments have demonstrated that a chamfer at the end of the cavity reliably allows the bubbles to escape to atmosphere. The existing reservoir 17 can be redesigned as illustrated in FIG. 20, where a modified cover 60, similar to that shown in FIG. 14, is shown with a chamfer 61 to assist in releasing bubbles, without affecting the even fluid flow through the cavity 18. The chamfer forms a first angled section 62 at about 60° relative to the cavity and slide surface.

Fluid evaporation rate is, however, directly linked to the surface area of the fluid exposed to atmosphere—a larger surface area will evaporate faster, and require more frequent replenishment. If the bubble escape angle is steep, the evaporation rate will increase.

This problem can be overcome by using two angles—a shallow angled section at, say, 15° between the cavity and the chamfer, to minimise evaporation, leading into the steeper angle for bubble release, which also serves to increase the volume of the reservoir.

The cover 60 is also provided with a second, identically shaped reservoir 63 at an opposite end thereof. The second reservoir 63 can also be used to replenish fluid within the cavity during heating and to allow bubbles to escape. The second reservoir 63 thereby allows for increased control of fluid conditions within the reaction chamber.

The embodiments of FIGS. 14 and 20 are considered to represent what is currently believed to be the best known method of performing the cover aspect of the invention.

The invention claimed is:

1. A cover for a microscope slide, said cover comprising: a planar body with a cavityed face and an opposed face, two side walls flanking the cavityed face, two legs that extend out from the side walls on the cavityed face and that are not in contact with the opposing face, and a locater attached to the planar body;
wherein the planar body is configured to slideably engage the microscope slide so that the cavityed face is parallel to the planar surface of the microscope slide and so that the side walls support the cover on the microscope slide;
wherein the locater can be used to slideably move the cavityed face parallel to a planar surface of the microscope slide;
wherein the planar body has a front end and a distal end and is shaped so that the front end extends upwardly and away from the cavityed face toward the opposed face to form a projection;
wherein the opposed face is sized so as to cover less than the whole length of the planar surface of the microscope slide; and
wherein when the cover is engaged with the microscope slide, (1) a cavity is defined by the cavityed face, the two side walls and the portion of the microscope slide engaged with the side walls, and (2) a reservoir is defined by the projection, the legs, and the portion of the microscope slide not engaged by the side walls.

2. The cover of claim 1, wherein when formed, the cavity's volume is between 20 and 300 microliters.

3. The cover of claim 1, wherein the projection is defined by a first section, angled at least at substantially 60° relative to the cavity, and a second section, positioned between the cavity and the first section, and orientated at a reduced angle relative to the cavity, as compared to the first section.

4. The cover of claim 3, wherein the second section is angled at least at substantially 15°.

5. The cover of claim 1, wherein the cover is made from a polymer material.

6. The cover of claim 5, wherein the cavity includes a coating of reduced surface roughness than the polymer material.

7. The cover of claim 1, wherein the cavity includes a coating with reduced porosity.

8. The cover of claim 1, wherein the cavity has one or more coatings.

9. The cover of claim 8, wherein a first coating is a material having similar properties to the material of the slide.

10. The cover of claim 9, wherein the first coating is silicon dioxide.

11. The cover of claim 9, wherein a second coating is placed intermediate a first coating to provide improved contact properties between the cover and first coating.

12. The cover of claim 1, wherein the cavity is substantially planar.

13. The cover of claim 1, wherein the reservoir is further defined between the projection, and legs attached to the side walls and which extend beyond the frontal end.

14. The cover of claim 1, wherein the cavity extends to the distal wall of the cover adjacent the locator.

15. The cover of claim 1, wherein when the cover is engaged with the microscope slide, the reservoir is sized to 150% of the volume of the cavity.

16. The cover of claim 1, wherein the cavity extends the full width of a sample holding region of the microscope slide.

17. The cover of claim 1, wherein a protrusion extends from the projection, to assist in wicking fluid into the reservoir.

18. The cover of claim 1, further comprising wing structures attached to the planar body configured to allow the cover to be engaged and pivoted relative to the microscope slide so as to open the cavity and allow the slide to be cleared of fluid.

19. A combination of a microscope slide, and a cover as claimed in claim 1, wherein the cavity of the cover is arranged to face the microscope slide so as to form a reaction chamber.

20. The combination of claim 19, wherein the reservoir is sized to 150% of the volume of the cavity.

21. The combination of claim 19, wherein the cavity's volume is between 20 and 300 microliters.

22. A method of treatment of a sample on a sample holding region of a microscope slide, comprising locating the cover of claim 1, over the slide, so that the cavity of the cover faces the slide to form a reaction chamber over the sample holding region, and depositing fluid into the fluid reservoir to allow the fluid to be drawn into the reaction chamber.

23. A method as claimed in claim 22, further comprising sliding the cover relative to the microscope slide to vary a degree of overlap between the cover and the sample holding region, which results in a corresponding variation in the reaction chamber volume.

24. A method as claimed in claim 22, wherein the cover further comprises wing structures attached to the planar body configured to allow the cover to be engaged and pivoted relative to the microscope slide and further comprising sliding the cover relative to the microscope slide until the wing structures are engaged and lifted relative to the microscope slide to pivot the cover into an open condition, thereby allowing fluid to drain from the reaction chamber.

25. A cover for a microscope slide, said cover comprising:
 a body defining a cavity when positioned over the microscope slide to form a reaction chamber, said body including a bottom surface and longitudinally extending side walls which support the body such that a space of a first height is provided between a top surface of the slide and the bottom surface of the body, said space defining the cavity;
 a projection extending from a first end of the body and laterally across a width of the body and being positioned above the bottom surface of the body to define a fluid reservoir with the top surface of the microscope slide when positioned over the slide, said fluid reservoir having a second height greater than the first height where the second height is corresponds to a distance from the top surface of the slide to a bottom surface of the projection, the fluid reservoir being separate from and in fluid communication with the cavity;
 an outlet at a second end of the cover distal from the first end; and
 a locator for controlling and locating the cover.

* * * * *